United States Patent [19]

Eberhard

[11] Patent Number: 5,325,296

[45] Date of Patent: Jun. 28, 1994

[54] STEP SIZE IN COMPLETE DATA SCANNING PATH FOR THREE DIMENSIONAL COMPUTERIZED TOMOGRAPHY

[75] Inventor: Jeffrey W. Eberhard, Schenectady, N.Y.

[73] Assignee: General Electric Company, Schenectady, N.Y.

[21] Appl. No.: 992,673

[22] Filed: Dec. 18, 1992

[51] Int. Cl.$^5$ .......................................... G06F 15/00
[52] U.S. Cl. ........................ 364/413.15; 364/413.14; 364/413.19
[58] Field of Search ...................... 364/413.14, 413.15, 364/413.24, 413.19; 250/363; 378/108, 109

[56] References Cited

U.S. PATENT DOCUMENTS

| | | | |
|---|---|---|---|
| 4,752,691 | 6/1988 | Hawman | 250/363 |
| 4,907,157 | 3/1990 | Uyama et al. | 364/413.13 |
| 4,942,596 | 7/1990 | Eberhard et al. | 378/179 |
| 5,073,910 | 12/1991 | Eberhard et al. | 378/4 |
| 5,187,659 | 2/1993 | Eberhard | 364/413.15 |

OTHER PUBLICATIONS

"Quantitative Cone-Beam reconmstruction", Hui Hu et al., EPIE vol. 1092 Medical Imaging III: Image Processing (1989), pp. 492-501.

"The Dynamic Spatial Reconstructor", Robb et al., Journal of Medical Systems, vol. 4, No. 2, 1980, pp. 253-288.

"Practical Cone-Beam Algorithm", Feldkamp et al., J. Opt. Soc. Am. A/V vol. 1, No. 6, Jun. 1984, pp. 612-619.

"Convolutional Reconstruction From Cone-Beam Projection Data", G. N. Minerbo, IEEE Transaction on Nuclear Science, vol. NS-26, No. 2, Apr. 1979, pp. 2682-2684.

"An Inversion Formula for Cone-Beam Reconstruction", H. K. Tuy, Siam J. Appl. Math., vol. 43, No. 3, Jun. 1983, pp. 545-552.

"Image Reconstruction from Cone-Beam Projections: Necessary and Sufficient Conditions and Reconstruction Methods", Bruce D. Smith, IEEE Transactions on Medical Imaging, vol. MI-4, No. 1, Mar. 1985, pp. 14-25.

"Iterative Three-Dimensional Reconstructional from Twin-Cone Beam Projections", M. Schlindwein, IEEE Transactions on Nuclear Science, vol. NS-25, No. 5, Oct. 1978, pp. 1135-1143.

"Algebraic Reconstruction Techniques (ART) for Three-Dimensional Electron Microscopy and X-Ray Photography", Gordon et al., J. Theor. Biol. (1970) 29, pp. 471-481.

"Tomographic Reconstruction from Experimentally Obtained Cone-Beam Projections", Webb et al., IEEE Transactions on Medical Imaging, vol. M1-6, No. 1, Mar. 1987, pp. 67-73.

"Cone-Beam Tomography: Recent Advances and a Tutorial Review", Bruce D. Smith, Optical Engineering, May 1990, vol. 29, No. 5, pp. 524-534.

"Analysis of a 3D Imaging System by Reconstruction from X Radiographies in Conical Geometry", Pierre Grangeat, Doctoral Thesis, pp. 1-303.

*Primary Examiner*—Roy N. Envall, Jr.
*Assistant Examiner*—Khai Tran
*Attorney, Agent, or Firm*—Paul R. Webb, II

[57] ABSTRACT

A technique for selecting discrete data acquisition points in three-dimensional computerized tomograph (3D CT) is based upon the center-to-center distances between detector elements in an area detector used for detecting images. The data acquisition points are selected to avoid excess computer power for processing redundant data and, at the same time, insure that a sufficient number of data points are used to minimize distortion and/or artifacts.

27 Claims, 2 Drawing Sheets

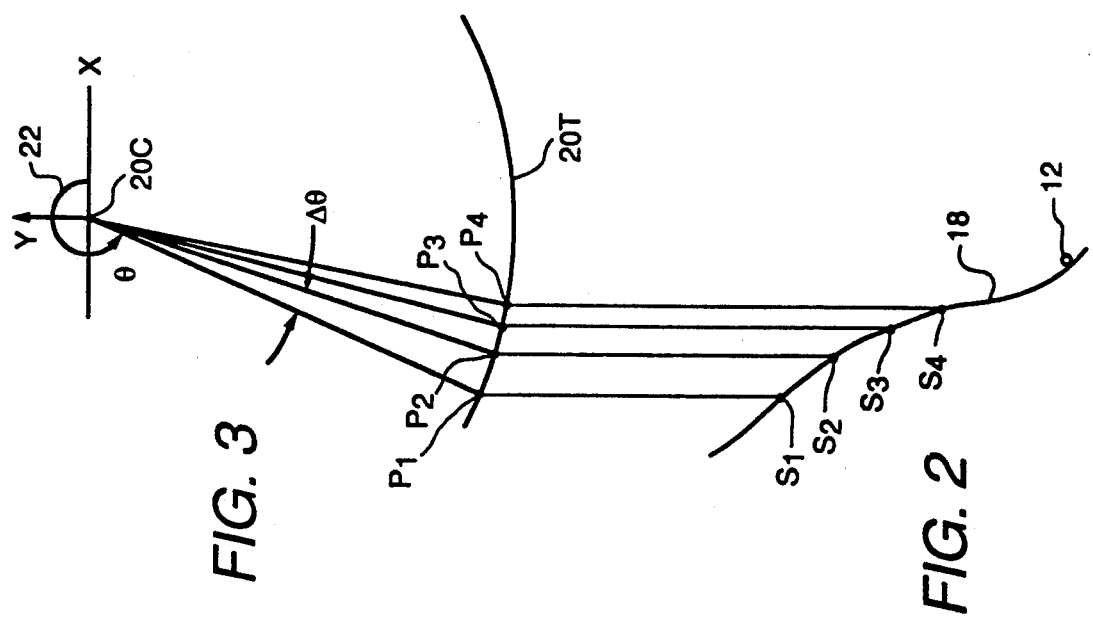
FIG. 3
FIG. 2
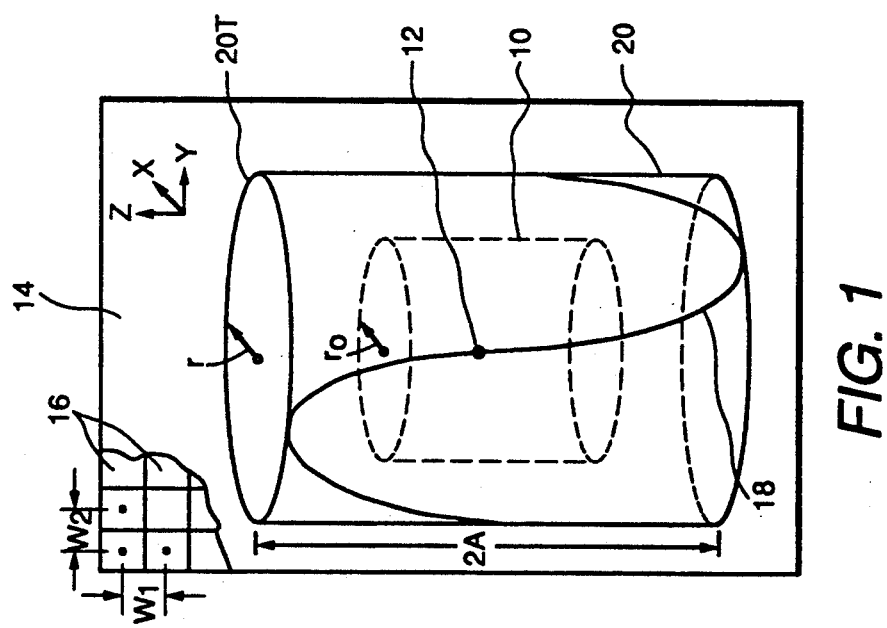
FIG. 1

STEP SIZE IN COMPLETE DATA SCANNING PATH FOR THREE DIMENSIONAL COMPUTERIZED TOMOGRAPHY

BACKGROUND OF THE INVENTION

The present invention relates to three-dimensional (3D) computerized tomography (CT) and, more particularly, methods and systems providing an appropriate step size in a complete data scanning path for cone beam CT.

In conventional computerized tomography for both medical and industrial applications, an x-ray fan beam and a linear array detector are employed. Two-dimensional (2D) imaging is achieved. While the data set is complete and image quality is correspondingly high, only a single slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal, because the distance between slices is typically less than the x-ray collimator aperture, resulting in a double exposure to many part of the body.

In 2D CT, the scanning path of the source is often a simple circular scan about the object. The linear array detector is fixed relative to the source. (Although it is usual to talk about a scan path of a source relative to the object to be imaged, it is to be appreciated that the object may be rotated or otherwise moved to provide relative motion between the object and the source). The data from the linear array detector is acquired at uniform angular intervals $\Delta\Theta$. For a system with a center-to-center separation between adjacent detectors of $\Delta w$, a field of view radius r and magnification M, $\Delta\Theta$ is typically chosen to be $$\Delta\Theta = (\Delta w/M)/r$$

This choice simply corresponds to the fact that for data acquired at two adjacent view angles spaced by $\Delta\Theta$ to be independent, a point on the circumference of the object (distance r from the center) must move from in front of one detector element to in front of the adjacent detector element $$\left(\text{a distance } \frac{\Delta w}{M}\right)$$

between view angles.

In a system employing true cone beam geometry fro 3D imaging, a cone beam x-ray source and a 2D area detector are used. An object is scanned, preferably over a 360° angular range, either be moving the x-ray source in a scanning circle around the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects, with improved dose utilization.

The standard scanning path used in cone beam 3D CT imaging is a single circle scan of source and detector around the object. The detector is typically sampled at uniform angular intervals around the circle as in 2D CT. However, the data acquired in a single scanning circle can be shown to be incomplete for 3D CT imaging.

Complete data scanning paths are known, but the paths are not confined to a single plane making the proper choice of a sample interval significantly different from that in the 2D or 3D circular scan case. U.S. Pat. No. 5,073,910 issued Dec. 17, 1991 to the present inventor and Hedengren discloses a complete data scanning path. The patent, which is assigned to the present assignee, is hereby incorporated by reference.

The criteria for data set completeness relative to scanning path in a 3D CT system are described in the paper by Bruce D. Smith entitled "Image Reconstruction From Cone-Beam Projections: Necessary and Sufficient Conditions and Reconstruction Methods", IEEE Transactions on Medical Imaging, Volume MI-4, No. 1, pages 14–25 (March 1985), hereby incorporated by reference.

Whether or not a non-planar scan path for cone beam 3D CT is complete path, locations in the scan path must be identified for acquiring data by the area detector. The source may be moved continuously with data being acquired from the area detector at different locations. Generally, the speed of data acquisition is relatively high compared to the movement of the source such that the small amount of movement of the source during the data acquisition will not introduce unacceptable effects. The data acquisition may be thought of as somewhat similar to use of high speed film to take a photograph of a moving object. If the film and shutter speed are sufficiently fast relative to the movement of the object, the film will show the object to be essentially stationary.

As an alternative to continuous motion scanning, one could use step wise scanning. In step wise scanning, one would move the source relative to the object being imaged, acquire data from the area detector while there is no relative motion between the object and the source, and move the source relative to the object after data acquisition is complete for a given location. The source is then stopped at a second location for data acquisition, data is then acquired, and the source is moved on to a third location for data acquisition and so forth.

Whether the relative motion of the source to the object occurs in a continuous fashion or the motion occurs in a step wise fashion as described, one should determine the locations in the trajectory at which data should be acquired. If the intervals $\Delta s$ in the trajectory s are relatively small, one can obtain the most accurate image. However, making the intervals $\Delta s$ relatively small will result in obtaining a large amount of redundant data. That is, the data from one data acquisition point in the trajectory s will have a significant overlap with the data from the area detector at the adjacent data acquisition point in the trajectory. More importantly, using especially small intervals $\Delta s$ requires a relatively large amount of computer processing power. That is, real-time processing of data becomes more difficult as the stream of data increases from use of smaller intervals $\Delta s$ in the trajectory s. Furthermore, it is hard to justify the extra cost to obtain the necessary computer processing power to process data corresponding to relatively small intervals $\Delta s$ if the data has a relatively high level of redundancy.

In either the continuous motion or step wise motion scan technique, one can reduce the requirements for data processing power by increasing the size of the intervals $\Delta s$ separating adjacent data acquisition points in the trajectory s. However, if the intervals $\Delta s$ between data acquisition points in the trajectory s are too large, independent or nonredundant data will be lost and artifacts and/or distortions will be introduced into the image data.

OBJECTS AND SUMMARY OF THE INVENTION

Accordingly, it is a primary object of the present invention to provide improved 3D CT imaging.

A more specific object of the present invention is to provide proper step size in intervals between data acquisition points in the trajectory of a source used for CT imaging.

Yet another object of the present invention is to provide CT imaging with a minimal amount of distortion and artifacts.

A still further object of the present invention is to provide CT imaging without requiring excessive compute power and data storage capacity.

The above and other objects of the present invention which will become more apparent as the description proceeds are realized by a scanning and data acquisition method for 3D CT imaging of a field of view containing at least a portion of an object illuminated by a source of imaging energy. The source is moved relative to the object (i.e., there is relative motion between the source and the object whichever is moved) in a non-planar source scanning trajectory s such that imaging energy passes through the portion of the object. A differential of s satisfies the relationship $ds^2 = dx^2 + dy^2 + dz^2$ where dx, dy, and dz are respectively differentials relative to orthogonal x, y, and z axes. Intervals $\Delta s$ are determined in the trajectory s for locations at which data corresponding to imaging energy sensed by a two-dimensional area detector is to be acquired. The detector has detector elements spaced center-to-center $w_1$ in a row direction and $w_2$ in a column direction perpendicular to the row direction. The intervals $\Delta s$ are determined according to equation I as follows:

$$\Delta s = k \cdot (1/2(w_1^2 + w_2^2))^{\frac{1}{2}} \left( \frac{r}{r_o} - \frac{1}{M} \right)$$

where r is the radius of the source scan path, $r_o$ is the radius of the field of view, M is the system magnification, k is a constant and $10 \geq k \geq 1/10$. As used herein, the exponential power of $\frac{1}{2}$ is used for square roots instead of using square root symbols. Data is then acquired at the intervals $\Delta s$ by using the detector to detect imaging energy which is passed through the portion of the object. A CT image is then displayed based on the acquired data.

More specifically, k has a value such that $4 \geq k \geq \frac{1}{4}$. Even more specifically, $(2)^{\frac{1}{2}}$ is $\geq k \geq 1/(2)^{\frac{1}{2}}$. Even more particularly, k would be between 0.9 and 1.1. Most particularly, k would equal 1.

In the preferred embodiment, $w_1 = w_2$ such that equation I simplifies to equation II as follows:

$$\Delta s = k \cdot w_1 \left( \frac{r}{r_o} - \frac{1}{M} \right)$$

and wherein the determination step uses equation II to determine the integrals $\Delta s$.

In one embodiment, the trajectory is a two cycle sinusoid on cylinder scan defined by equations III as follows:

$$x = r \cos \Theta$$

$$y = r \sin \Theta$$

$$z = A \sin 2\Theta$$

where r and A are respectively the radius and one half the height of the cylinder and $\Theta$ is an angle within an xy plane of point on the trajectory relative to the x axis such that equation II simplifies to equation IV as follows:

$$\Delta \Theta = k \cdot w_1 \left( \frac{r}{r_o} - \frac{1}{M} \right) / (r^2 + 4A^2 \cos^2 2\Theta)^{\frac{1}{2}}$$

where values of $\Delta \Theta$ represent angular intervals relative to $\Theta$ at which data is to be acquired, and wherein the determining step uses equation IV or a simplified version of equation IV to calculate values for $\Delta \Theta$ which values correspond to $\Delta s$, and wherein data is acquired at angular intervals $\Delta \Theta$. If A = r such that equation IV simplifies to equation V as follows:

$$\Delta \Theta = k \cdot w_1 \left( \frac{r}{r_o} - \frac{1}{M} \right) / (r(1 + 4\cos^2 2\Theta)^{\frac{1}{2}})$$

the determining step uses equation V to calculate values for $\Delta \Theta$.

If the trajectory s is parameterized by general trajectory equations as follows:

$$x = f_x(u)$$

$$y = f_y(u)$$

$$z = f_z(u)$$

where u is a parameter used to define the trajectory, $f_x$, $f_y$, and $f_z$ are functions of u, and the intervals $\Delta s$ are determined by providing $\Delta u$, which are changes in the parameter u corresponding to the intervals $\Delta s$, using $$\Delta u = \frac{k \cdot (1/2(w_1^2 + w_2^2))^{\frac{1}{2}} \left( \frac{r}{r_o} - \frac{1}{M} \right)}{(F_x^2(u) + F_y^2(u) + F_z^2(u))^{\frac{1}{2}}}$$

where $F_x$, $F_y$, and $F_z$ are respectively the derivative functions relative to u of $f_x$, $f_y$, and $f_z$.

In another embodiment, the trajectory s is on a cylinder of radius r and is defined by:

$$x = r \cos \Theta$$

$$y = r \sin \Theta$$

$$z = f(\Theta)$$

where $\Theta$ is an angle within an xy plane of a point on the trajectory relative to the x axis such that the intervals $\Delta s$ are determined by providing angular intervals $\Delta\Theta$ according to:

$$\Delta\Theta = \frac{k \cdot (1/2(w_1^2 + w_2^2))^{\frac{1}{2}} \left(\frac{r}{r_o} \cdot \frac{1}{M}\right)}{(r^2 + F^2(\Theta))^{\frac{1}{2}}}$$

where F is the derivative function relative to $\Theta$ of f and wherein data is acquired at the angular intervals $\Delta\Theta$.

In another embodiment, the trajectory s is on a sphere of radius r and is defined by:
$x = r \cdot (1 - \frac{1}{3} \sin^2 2\Theta)^{\frac{1}{2}} \cos\Theta$
$y = r \cdot (1 - \frac{1}{3} \sin^2 2\Theta)^{\frac{1}{2}} \sin\Theta$
$z = r/(3)^{\frac{1}{2}} \sin 2\Theta$ where $\Theta$ is an angle within the xy plane of a point on the trajectory relative to the x axis such that the intervals $\Delta s$ are determined by providing angular intervals $\Delta\Theta$ according to:

$$\Delta\Theta = \frac{k \cdot (1/2(w_1^2 + w_2^2))^{\frac{1}{2}} \left(\frac{r}{r_o} \cdot \frac{1}{M}\right)(1 - 1/3\sin^2 2\Theta)^{\frac{1}{2}}}{r(1/3 + 2\cos^2 2\Theta + 1/9 \cdot \sin^4 2\Theta)^{\frac{1}{2}}}$$

and wherein data is acquired at the angular intervals $\Delta\Theta$.

In another embodiment, the trajectory s is a helical scan path defined by:

$x = r \cos\Theta$ $y = r \sin\Theta$ $z = \Theta \cdot h/2\pi$ where r and h are constants, $\pi$ is the circumference of a circle divided by its diameter, and $\Theta$ is an angle within the xy plane of a point on the trajectory relative to the x axis such that the intervals $\Delta s$ are determined by providing angular intervals $\Delta\Theta$ according to:

$$\Delta\Theta = \frac{k \cdot (1/2(w_1^2 + w_2^2))^{\frac{1}{2}} \left(\frac{r}{r_o} \cdot \frac{1}{M}\right)}{(r^2 + (h/2\pi)^2)^{\frac{1}{2}}}$$

and wherein data is acquired at the angular intervals $\Delta\Theta$.

The three-dimensional computerized tomography system according to the present invention includes a source of imaging energy for illuminating at least a portion of an object to be imaged. A two-dimensional area detector having detector elements spaced center-to-center $w_1$ in a row direction and $w_2$ in a column direction perpendicular to the row direction is positioned to receive imaging energy from the source. A scanning means causes relative motion of the source and the object such that the source moves along a non-planar scanning trajectory s relative to the object. A square of a differential of s satisfies the relationship $ds^2 = dx^2 + dy^2 + dz^2$ where dx, dy, and dz are respectively differentials relative to orthogonal x, y, and z axes. The system further includes a means for determining intervals $\Delta s$ in the trajectory s for locations at which data corresponding to imaging energy sensed by the area detector is to be acquired. The values for $\Delta s$ are determined according to equation I as follows:

$$\Delta s = k \cdot (1/2(w_1^2 + w_2^2))^{\frac{1}{2}} \left(\frac{r}{r_o} \cdot \frac{1}{M}\right)$$

where k is a constant and $10 \geq k \geq 1/10$. A means, operatively connected to the area detector acquires data from the area detector at intervals $\Delta s$. A display is operatively connected to the means for acquiring data for displaying a CT image based on the acquired data. The system is used for carrying out the various methods and using the various trajectories as described above. The means for determining is a memory containing data representative of locations in trajectory s corresponding to the intervals $\Delta s$. Thus, the data may have been previously calculated according to the relationships described above. In an alternate embodiment, the means for determining is operable to calculate data representative of locations in the trajectory s corresponding to the intervals $\Delta s$.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 1 is a perspective illustrating a trajectory of a cone beam source relative to an area detector;

FIG. 2 shows a portion of the trajectory with several data acquisition points illustrated;

FIG. 3 shows a projection of the trajectory of FIG. 2 into an xy plane; and

DETAILED DESCRIPTION OF THE INVENTION

Figure 4:
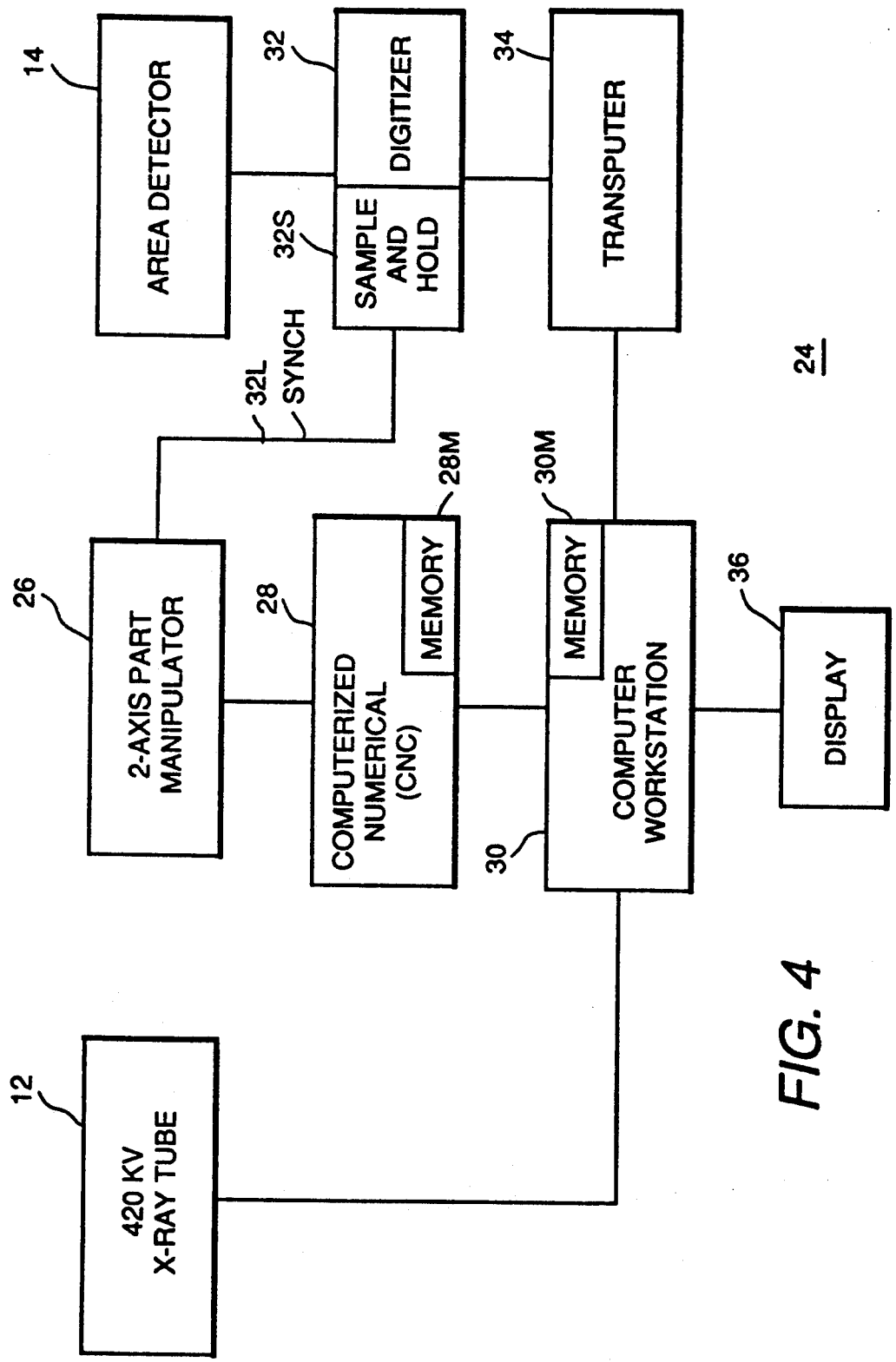
FIG. 4 is a simplified block diagram illustrating the major components of the system according to the present invention.

As shown in FIG. 1, an object 10 which is to be imaged is disposed between a source 12 and an area detector 14. The area detector 14 is illustrated as planar, but non-planar area detectors might alternately be used. The area detector 14 is a two-dimensional array of detector elements 16 arranged in rows having a center-to-center spacing of $w_1$ and columns having a center-to-center spacing of $w_2$. For ease of illustration, only a few of the detector elements 16 are shown in the upper left of the generally rectangular area detector 14, but it will be understood that the detector elements 16 would extend over the extent of area detector 14. In the arrangement of FIG. 1, the detector elements 16 are square and $w_1 = w_2$, but other arrangements might be used.

The arrangement of FIG. 1 is used to generate a CT image of the object 10 under test. The object 10, which is simply illustrated as a cylinder in FIG. 1, may be a work piece which is to be checked for flaws or it may be a human or animal patient which is to be checked for medical purposes.

The source 12 will move along the trajectory 18 relative to the object 10. Describing the trajectory 18 as an arc of length s, a distance along the trajectory or arc is given by $$ds^2 = dx^2 + dy^2 + dz^2 \quad (1)$$

The present inventor proposes that, for the general arc trajectory of length s, the steps $\Delta s$ in between different data acquisition points be related to the center-to-center distance between different detector elements 16 in the area detector 14. Further, the present inventor proposes that, for the case where $w_1 = w_2$, the steps between adjacent data acquisition points should be proportional to the center-to-center distance $w_1$. Thus, the following relationship should be realized:

$$\Delta s = k \cdot (1/2(w_1^2 + w_2^2))^{\frac{1}{2}} \left( \frac{r}{r_0} \frac{1}{M} \right) \quad (2)$$

where k is a constant and r, $r_0$ and M are as previously defined. It will be readily appreciated that the above equation reduces to equation 3 as follows when $w_1 = w_2$:

$$\Delta s = k \cdot w_1 \left( \frac{r}{r_0} \frac{1}{M} \right) \quad (3)$$

Equations 2 and 3 above represent the relationship between the step size between data acquisition points and the center-to-center distances between adjacent detector elements. Most particularly, the value of k will be 1. The reason for that is that, for example, assuming that $\Delta s$ is parallel to the x axis upon part of the curve or trajectory s for the sake of simplicity, when the position along arc or trajectory s has changed by $w_1$ (assuming square detector elements such that equation 3 above applies), a point on the object will have moved from in front of one detector to in front of another detector. More generally, $1.1 \geq k \geq 0.9$. More generally again, k may have a value less than or equal to the square root of 2 and greater than or equal to the square root of $\frac{1}{2}$. Even more generally, k should have a value of less than or equal to and greater than or equal to $\frac{1}{4}$. In its broadest aspects, the present invention contemplates k having a value of less than or equal to 10 and greater than or equal to 1/10.

In FIG. 1, the trajectory 18 is illustrated as a two cycle sinusoid on cylinder scan. In particular, the trajectory 18 is disposed on the cylinder 20 having a radius r and a height of 2A. This trajectory 18 or s constitutes a complete scan path in accord with the criteria explained in the incorporated by reference documents. With reference to the orthogonal x, y, and z axes shown in the upper right of FIG. 1, the equations of trajectory 18 are as follows:

$x = r \cos \Theta$ $y = r \sin \Theta$ $z = A \sin 2\Theta \quad (4)$ where $\Theta$ is an angle within an xy plane of a point on the trajectory relative to the x axis. The meaning of $\Theta$ is the usual meaning in a cylindrical coordinate system and may also be understood with reference to FIGS. 2 and 3. FIG. 2 shows a portion of the trajectory s having data acquisition points $s_1$, $s_2$, $s_3$, and $s_4$. FIG. 3 shows a top view looking down upon the top edge 20P of cylinder 20 and illustrating projection $p_1$, $p_2$, $p_3$, and $p_4$ corresponding to projections of points $s_1$, $s_2$, $s_3$, and $s_4$. The value for $\Theta$ of $s_1$ is illustrated at 22 relative to the x axis. Note that the origin for the x, y, and z axes would be 20C which would be disposed in the center of the cylinder 20.

Changing from the differential ds to the difference $\Delta s$ in equation 1 and substituting the right side of equation 2 for $\Delta s$, equation 1 may be rewritten as:

$$k^2 \cdot (1/2(w_1^2 + w_2^2)) \left( \frac{r}{r_0} \frac{1}{M} \right)^2 = dx^2 + dy^2 + dz^2 \quad (5)$$

Substituting for the differentials with respect to x, y, and z in equation 5 and using the well known trig identity that $\cos^2\Theta + \sin^2\Theta = 1$, equation 6 is derived as follows:

$$k^2 \cdot (1/2(w_1^2 + w_2^2)) \left( \frac{r}{r_0} \frac{1}{M} \right)^2 = (r^2 + 4A^2\cos^2 2\Theta)d\Theta^2 \quad (6)$$

Substituting the angular change $\Delta\Theta$ for the differential $d\Theta$, rearranging equation 6, and taking the square root of both sides, results in equation 7 as follows:

$$\Delta\Theta = k \cdot (1/2(w_1^2 + w_2^2))^{\frac{1}{2}} \left( \frac{r}{r_0} \frac{1}{M} \right) / (r^2 + 4A^2\cos^2 2\Theta)^{\frac{1}{2}} \quad (7)$$

If $w_1 = w_2$, then equation 7 simplifies to equation 8 as follows:

$$\Delta\Theta = k \cdot w_1 \left( \frac{r}{r_0} \frac{1}{M} \right) / (r^2 + 4A^2\cos^2 2\Theta)^{\frac{1}{2}} \quad (8)$$

where A=r, equation 8 simplifies to:

$$\Delta\Theta = k \cdot w_1 \left( \frac{r}{r_0} \frac{1}{M} \right) / (r^2(1 + 4\cos^2 2\Theta)^{\frac{1}{2}}) \quad (9)$$

Equations 7, 8 and 9 give values of angular change $\Delta\Theta$ to determine when data acquisition should be performed along the trajectory 18.

With reference now to FIGS. 2 and 3, as the source 12 moves from data acquisition points $s_1$, the angle $\Theta$ will increase by $\Delta\Theta$ until the next data acquisition point $s_2$ is obtained. The angles are shown in FIG. 3 only. Assuming that the angle $\Theta$ illustrates in FIG. 3 for data acquisition points $s_1$ is 165°, the appropriate one of equations 7, 8 or 9 could be used to obtain a value of $\Delta\Theta$. When the source 12 had moved to a point $s_2$ having an angle $\Theta$ which equaled the previous value of $\Theta$ plus the calculated $\Delta\Theta$, data acquisition would again be initiated. The next value for $\Delta\Theta$ would be calculated using the angle corresponding to projection $p_2$ and the iterative process would be repeated. Note that although $\Delta s$ is constant, the value $\Delta\Theta$ between different of the data acquisition points and their projections may vary significantly depending upon the relative rates of change of the trajectory s. If the rate of change of s relative to the z direction is relative high, the $\Delta\Theta$ values will be relatively low. At other places in the path where the rate of change with respect to the z direction is relatively low, the angular change $\Delta\Theta$ will be relatively high.

Equations 4 through 9 above relate to the specific scanning trajectory corresponding to a two cycle sinusoid on cylinder, but it should be emphasized that equations 2 and 3 above may be used in a more general case to calculate the intervals between data acquisition points in any trajectory. Although the present invention is especially well suited for calculating the step sizes for a complete data scanning path, the present invention may also be used for determining step sizes between data acquisition points for an incomplete data scanning path.

In a general case where a trajectory s is parameterized by general trajectory equations as follows:

$$x = f_x(u)$$
$$y = f_y(u) \quad (10)$$
$$z = f_z(u)$$

where u is $$\Delta u = \frac{k \cdot (1/2(w_1^2 + w_2^2))^{\frac{1}{2}} \left(\frac{r}{r_o} - \frac{1}{M}\right)}{(F_x^2(u) + F_y^2(u) + F_z^2(u))^{\frac{1}{2}}} \quad (11)$$

where $F_x$, $F_y$, and $F_z$ respectively are derivative functions with respect to u of $f_x$, $f_y$, and $f_z$. Thus, equation 11 gives a general manner of calculating $\Delta u$, the changes in a parameter, between data acquisition points. In different situations, this may be simpler than calculating $\Delta s$ directly.

It will be readily appreciated that in the case where the source 12 is moving at a constant speed such that the parameter $u=t$, the time, the data will be acquired at uniform time intervals $\Delta t$ which correspond to the right hand side of the equation 11 above. Of course, in the more general case, $\Delta u$ is not necessarily a constant and may have different values as explained above with respect to the different possible values of $\Delta\Theta$ depending upon the value of $\Theta$ corresponding to the illustration of FIGS. 2 and 3.

In a general case of a trajectory s on a cylinder of radius r and defined by equation 12 as follows:

$$x = r\cos\Theta$$
$$y = r\sin\Theta \quad (12)$$
$$z = f(\Theta)$$

where $\Theta$ is defined as in the example of FIG. 1 and f is a function of $\Theta$. The differentials of x, y, and z may be taken from equation 12 and substituted into equation 1 and ds replaced by the right hand side of equation 2 above. Knowing also that $\sin^2\Theta + \cos^2\Theta = 1$, it will readily follow that the intervals $\Delta s$ may be determined by calculating angular intervals $\Delta\Theta$ according to:

$$\Delta\Theta = \frac{k \cdot (1/2(w_1^2 + w_2^2))^{\frac{1}{2}} \left(\frac{r}{r_o} - \frac{1}{M}\right)}{(r^2 + F^2(\Theta))^{\frac{1}{2}}} \quad (13)$$

where F is the derivative function of f relative to $\Theta$.

For a helical scan path wherein x, y, and z are given by equations 14 as follows:

$$x = r\cos\Theta$$
$$y = r\sin\Theta \quad (14)$$
$$z = \Theta \cdot h/2\pi$$

where r and h are constants, $\pi$ is the circumference of a circle divided by its diameter, and $\Theta$ is the cylindrical coordinate. Substituting the right hand side of equation 2 for the left hand side of equation 1 and substituting the differentials of equation 14 into the right hand side of equation 1, substituting $\Delta\Theta$ for the differential of $\Theta$, using the trig identity that $\sin^2\Theta + \cos^2\Theta = 1$, and rearranging indicates that the intervals $\Delta s$, may be determined by calculating angular intervals $\Delta\Theta$ according to equation 15 as follows:

$$\Delta\Theta = \frac{k \cdot (1/2(w_1^2 + w_2^2))^{\frac{1}{2}} \left(\frac{r}{r_o} - \frac{1}{M}\right)}{(r^2 + (h/2\pi)^2)^{\frac{1}{2}}} \quad (15)$$

Another complete trajectory or data scan path according to the criteria established by the incorporated by reference documents is a trajectory on a sphere of radius r defined by equations 16 as follows:

$$x = r\cos\Theta(1 - 1/3 \cdot \sin^2 2\Theta)^{\frac{1}{2}}$$
$$y = r\sin\Theta(1 - 1/3 \cdot \sin^2 2\Theta)^{\frac{1}{2}} \quad (16)$$
$$z = r/(3)^{\frac{1}{2}} \sin 2\Theta$$

where $\Theta$ is an angle within the xy plane of a point on the trajectory relative to the x axis (the same as defined with respect to FIGS. 1-3 in the discussion above). Substituting differentials of the right hand side of equation 16 above for the right hand side of equation 1 and substituting the right hand side of equation 2 for the value ds in equation 1, replacing $d\Theta$ by $\Delta\Theta$, using the trig identity that $\sin^2 2\Theta + \cos^2 2\Theta = 1$, indicates that the angular intervals $\Delta\Theta$ between adjacent data acquisition points should be defined according to equation 17 as follows:

$$\Delta\Theta = \frac{k \cdot (1/2(w_1^2 + w_2^2))^{\frac{1}{2}}(1 - 1/3\sin^2 2\Theta)^{\frac{1}{2}} \left(\frac{r}{r_o} - \frac{1}{M}\right)}{r(1/3 + 2\cos^2 2\Theta + 1/9 \cdot \sin^4 2\Theta)^{\frac{1}{2}}} \quad (17)$$

Thus, using equation 17, the angular intervals from one acquisition data point to another may be determined in conformance with equation 2 above. Again, as discussed with respect to FIGS. 2 and 3 above, the value of $\Delta\Theta$ will change depending upon the value of $\Theta$ itself. This is necessary in order to maintain $\Delta s$ constant as required by equation 2 above.

It should be readily appreciated that in all of the above equations wherein $w_1$ and $w_2$ are given, the quantity $\frac{1}{2}(w_1^2 + w_2^2)^{\frac{1}{2}}$ may be replaced by $w_1$ for the case of square detector elements 16 where $w_1 = w_2$.

With reference now to FIG. 4, the system 24 according to the present invention includes a cone beam source 12 and area detector 14 as previously discussed. The cone beam source 12 could alternately be neutrons, positrons, or other form of radiation or electromagnetic energy from point source. Alternately, other forms of imaging energy might by used.

The area detector 14, which may be an image intensifier or Hi-Light area detector to convert x-ray radiation to visible light and to convert the visible light into an analog voltage when the source 12 is an x-ray source, detects whatever form of imaging energy is used in a particular application. For example, if the imaging energy was neutrons instead of x-ray, the area detector would of course be suitable for detecting neutrons.

A known two-axis part manipulator 26 is used to cause the relative scanning movement between the object (not shown in FIG. 4) which is to be imaged and the source 12. Additionally, the detector 14 would be fixed relative to the source 12 (i.e., if one moves, the other moves with it). Accordingly, the manipulator 26 may move the object 10 (FIG. 1 only), while the source 12 and detector 14 are stationary or it may move the source 12 and detector 14 while the object is stationary. For purposes of the discussion of the present application, it is assumed that the x, y, and z axes are fixed relative to the object 10 (FIG. 1 only) under test and that the source 12 is moved. However, this assumption is simply for ease of discussion and it will be readily understood that the trajectory steps may be determined using the present invention regardless of whether the object or source is doing the actual moving.

The manipulator 26 is controlled by a known computerized numerical controller 28, which may, for example, be a type made by Aerotech. The controller 28 may include a memory 28M having data defining the scan path in known fashion. Alternately, and also using well known techniques, the memory 30M of a computer workstation 30, which is connected to the controller 28, may have the data which defines movements of the manipulator 26 and therefore defines the scan path or trajectory. The computer work station 30 may be a work station made by Sun, although other computer work stations and possibly even personal computers might be used in place of the work station 30. The computer work station controls the other components of the system 24 in known fashion.

Connected to the area detector 14 is a digitizer 32. The digitizer 32 operates in known fashion to convert analog signals from the area detector into digital signals representative of the image of the object under test. The digitizer 32 may include sample and hold circuits 32S. The sample and hold circuits receive the analog signals from the area detector, one analog signal for each of the detector elements 16 (FIG. 1 only). When the source 12 is at a data acquisition point such as $s_1$, $s_2$, $s_3$, and $s_4$ (refer back momentarily to FIG. 2), the manipulator 26 (or controller 28) will send a synch signal on line 32L to the various sample and hold circuits within digitizer 32. The sample and hold circuits 32S will then hold the various analog signals received from the detector elements 16 within detector 14 and the analog signals would then be digitized by the remainder of the digitizer 32 in known fashion. The sample and hold circuits, which might be replaced by a frame grabber, serve as a means for acquiring data from the area detector 14 at intervals $\Delta s$.

The digitized values corresponding to the sensed radiation from each of the detector elements within detector 14 are supplied by the digitizer 32 to a transputer 34. Data could go to an alternate reconstruction computer or directly to the workstation. The transputer 34, which may be of a known commercially available type such as Meiko M40, is an array processor which provides the necessary signal processing for the signals coming from the digitizer 32. The transputer 34 may perform the necessary image processing such that a display might be connected directly to the transputer to display the images from the CT scan. However, in the alternate arrangement shown in FIG. 4, the processed data from transputer 34 is supplied to the computer work station 30 and the computer work station 30 supplies the data, with or without further processing, to the display 36.

As mentioned previously, at least one of the memories 28M or 30M will contain data defining the scan path or trajectory. Additionally, one of the memories 28M and 30M will include data representative of the intervals between data acquisition points. Those intervals may have been previously calculated based upon equation 2 above or any of the equations derived from it defining the intervals in terms of $\Delta\Theta$ or $\Delta u$. For example, assuming that equation 7 is being used for a two cycle sinusoid on cylinder trajectory, an initial value of $\Delta\Theta$ may be calculated based upon an initial value of $\Theta$ equal to 0. Therefore, the first data acquisition point may be for $\Theta$ equals 0 and the second data acquisition point may be for the value of $\Theta$ equal to the first calculated $\Delta\Theta$. Assuming that the second value for $\Delta\Theta$ equals 1.5°, data acquisition points corresponding to $\Theta$ values of 0°, 1°, and 2.5° have been established. The next value of $\Delta\Theta$ is calculated using a value of 2.5° or $\Theta$. This process is repeated until $\Theta$ has taken on values between 0° and 360°. If desired, known techniques might be used to slightly modify some of the intervals so that the data acquisition point after 360° of rotation will be the same as initially. For example, if $\Theta$ of 359° yields a value of 0.7° for $\Delta$", one might use two steps, each of 0.5°, in order to step from 359° back to 0° such that the same interval size might be used on each pass along the trajectory or scan path.

It will be readily understood that either of the memories 28M or 30M may contain data representative of data acquisition points corresponding to other trajectories. Indeed, the memories might contain various alternate scan paths together with the interval sizes for the scan paths, the interval sizes having been previously calculated according to the equations previously described. As used herein, memory shall include hardware memories as shown as well as floppy discs and other memory media on which data or programs relative to step size might be stored.

As an alternative to previously calculating the step or interval sizes for the scan paths or trajectories, either of the memories 28M or 30M may contain programs which calculate on a real-time basis the values for $\Delta\Theta$, $\Delta u$, or other variables allowing selection of data acquisition points corresponding to equation 2 above. The calculations are relatively straightforward.

Whether the memories 28M or 30M contain the actual interval sizes or simply contain a program which calculates the interval sizes as the source 12 proceeds along a trajectory, a synch signal would be generated by manipulator 26 (or controller 28 or computer work station 30) upon a data acquisition point being reached in the trajectory.

Although various specific constructions have been given for the present invention, it is to be understood that these are for illustrative purposes only. Various modifications and adaptation will be readily apparent to those of skill in the art. For example, although the present invention has been described with reference to a source which physically moves relative to the object during the scanning operation, an alternative is possible. In such an alternative, a material may be around or partially around the object to be viewed, which material generates imaging energy upon being struck by a different kind of energy beam. The beam applied to the source material causes the source material to in turn emit an imaging energy. Although the source is not physically moved relative to the object, the source would effectively be moved relative to the object by sweeping the beam striking the source material in a path corresponding to the trajectory. In similar fashion and as used herein, moving the source relative to the object shall include situations where a series of sources are turned on sequentially o effectively move the source as well as the beam striking a source material type of source movement. In view of these and other modifications, the scope of the present invention should be determined by reference to the claims appended hereto.

What is claimed is:

1. A scanning and data acquisition method for three-dimensional computerized tomography (CT) imaging of a field of view containing at least a portion of an object illuminated by a source of imaging energy, the method comprising the steps of:

producing imaging energy from said source;

moving the source relative to the object in a non-planar source scanning trajectory s such that the imaging energy passes through the portion of said object, and a square of a differential of s, $ds^2 = dx^2 + dy^2 + dz^2$ where dx, dy, and dz are respectively differentials relative to orthogonal x, y, and z axes;

determining intervals $\Delta s$ in the trajectory s for locations at which data corresponding to imaging energy sensed by a two-dimensional area detector is to be acquired, the detector having detector elements spaced center-to-center $w_1$ in a row direction and $w_2$ in a column direction perpendicular to the row direction, $\Delta s$ being determined according to equation I as follows:

$$\Delta s = k \cdot (1/2(w_1^2 + w_2^2))^{\frac{1}{2}} \left( \frac{r}{r_o} \quad \frac{1}{M} \right)$$

where r is the radius of the source scan path, $r_0$ is the radius of the field of view, M is the system magnification, k is a constant and $10 \geq k \geq 1/10$;

detecting imaging energy which has passed through said portion of said object, said detecting step performed by use of the detector;

acquiring data at the intervals $\Delta s$ from use of the detector; and displaying a CT image based on the acquired data.

2. The method of claim 1 wherein $4 \geq k \geq \frac{1}{4}$.

3. The method of claim 2 wherein $(2)^{\frac{1}{2}} \geq k \geq 1/(2)^{\frac{1}{2}}$.

4. The method of claim 3 wherein k=1.

5. The method of claim 1 wherein $w_1 = w_2$ such that equation I simplifies to equation II as follows:

$$\Delta s = k \cdot w_1 \left( \frac{r}{r_o} \quad \frac{1}{M} \right)$$

and wherein the determination step uses equation II to determine the integrals $\Delta s$.

6. The method of claim 5 wherein the trajectory is a two cycle sinusoid on cylinder scan defined by equations III as follows:

$x = r \cos \Theta$ $y = r \sin \Theta$ $z = A \sin 2\Theta$ where r and A are respectively the radius and one-half the height of the cylinder and $\Theta$ is an angle within an xy plane of a point on the trajectory relative to the x axis such that equation II simplifies to equation IV as follows:

$$\Delta \Theta = k \cdot w_1 \left( \frac{r}{r_o} \quad \frac{1}{M} \right) / (r^2 + 4A^2 \cos^2 2\Theta)^{\frac{1}{2}}$$

where values of $\Delta \Theta$ represent angular intervals relative to $\Theta$ at which data is to be acquired, and wherein the determining step uses equation IV or a simplified version of equation IV to calculate values for $\Delta s$ which values correspond to $\Delta s$, and wherein data is acquired at angular intervals $\Delta \Theta$.

7. The method of claim 6 wherein A=r such that equation IV simplifies to equation V as follows:

$$\Delta \Theta = k \cdot w_1 \left( \frac{r}{r_o} \quad \frac{1}{M} \right) / (r(1 + 4\cos^2 2\Theta)^{\frac{1}{2}})$$

and wherein the determining step uses equation V to calculate values for $\Delta \Theta$.

8. The method of claim 6 wherein $4 \geq k \geq \frac{1}{4}$.

9. The method of claim 8 wherein $(2)^{\frac{1}{2}} \geq k \geq 1/(2)^{\frac{1}{2}}$.

10. The method of claim 9 wherein $1.1 \geq k \geq 0.9$.

11. The method of claim 10 wherein k=1.

12. The method of claim 1 wherein the trajectory s is parameterized by general trajectory equations as follows:

$x = f_x(u)$ $y = f_y(u)$ $z = f_z(u)$ where u is a parameter used to define the trajectory, $f_x$, $f_y$, and $f_z$ are functions of u, and the intervals $\Delta s$ are determined by calculating $\Delta u$, which are changes in the parameter u corresponding to the intervals $\Delta s$, using $$\Delta u = \frac{k \cdot (1/2(w_1^2 + w_2^2))^{\frac{1}{2}} \left( \frac{r}{r_o} \quad \frac{1}{M} \right)}{(F_x^2(u) + F_y^2(u) + F_z^2(u))^{\frac{1}{2}}}$$

where $F_x$, $F_y$, and $F_z$ are respectively the derivative functions relative to u of $f_x$, $f_y$, and $f_z$.

13. The method of claim 1 wherein the trajectory s is on a cylinder of radius r and is defined by:

$x = r \cos \Theta$ $y = r \sin \Theta$ $z = f(\Theta)$ where f is a function of $\Theta$ and $\Theta$ is an angle within an xy plane of a point on the trajectory relative to the x axis such that the intervals 66 s are determined by providing angular intervals $\Delta\Theta$ according to:

$$\Delta\Theta = \frac{k \cdot (1/2(w_1^2 + w_2^2))^{\frac{1}{2}} \left(\frac{r}{r_o} - \frac{1}{M}\right)}{(r^2 F^2(\Theta))^{\frac{1}{2}}}$$

where F is the derivative function of f relative to $\Theta$ and wherein data is acquired at the angular intervals $\Delta\Theta$.

14. The method of claim 1 wherein the trajectory s is on a sphere of radius r and is defined by:

$$x = r \cdot (1 - \tfrac{2}{3} \sin^2 2\Theta)^{\frac{1}{2}} \cos \Theta$$

$$y = r \cdot (1 - \tfrac{2}{3} \sin^2 2\Theta)^{\frac{1}{2}} \sin \Theta$$

$$z = r/(3)^{\frac{1}{2}} \sin 2\Theta$$

where $\Theta$ is an angle within the xy plane of a point on the trajectory relative to the x axis such that the intervals $\Delta$s are determined by providing angular intervals $\Delta\Theta$ according to:

$$\Delta\Theta = \frac{k \cdot (1/2(w_1^2 + w_2^2))^{\frac{1}{2}}(1 - 1/3\sin^2 2\Theta)^{\frac{1}{2}} \left(\frac{r}{r_o} - \frac{1}{M}\right)}{r(1/3 + 2\cos^2 2\Theta + 1/9 \cdot \sin^4 2\Theta)^{\frac{1}{2}}}$$

and wherein data is acquired at the angular intervals $\Delta\Theta$.

15. The method of claim 1 wherein the trajectory s is a helical scan path defined by:

$$x = r \cos \Theta$$

$$y = r \sin \Theta$$

$$z = \Theta \cdot h/2\pi$$

where r and h are constants, $\pi$ is the circumference of a circle divided by the circle's diameter, and $\Theta$ is an angle within the xy plane of a point on the trajectory relative to the x axis such that the intervals $\Delta$s are determined by providing angular intervals $\Delta\Theta$ according to:

$$\Delta\Theta = \frac{k \cdot (1/2(w_1^2 + w_2^2))^{\frac{1}{2}} \left(\frac{r}{r_o} - \frac{1}{M}\right)}{(r^2 + (h/2\pi)^2)^{\frac{1}{2}}}$$

and wherein data is acquired at the angular intervals $\Delta\Theta$.

16. A three-dimensional computerized tomography (CT) system comprising:
   a source of imaging energy for illuminating at least a portion of an object to be imaged;
   a two-dimensional area detector having detector elements spaced center-to-center $w_1$ in a row direction and $w_2$ in a column direction perpendicular to the row direction is positioned to receive imaging energy from the source;
   scanning means causing relative motion of the source and the object such that the source moves along a non-planar scanning trajectory s relative to the object, a square of a differential of s $ds^2 = dx^2 + dy^2 + dz^2$ where dx, dy, and dz are respectively differentials relative to orthogonal x, y, and z axes;
   means for determining intervals $\Delta$s in the trajectory s for locations at which data corresponding to imaging energy sensed by said area detector is to be acquired where $\Delta$s is determined according to equation I as follows:

$$\Delta s = k \cdot (1/2(w_1^2 + w_2^2))^{\frac{1}{2}} \left(\frac{r}{r_o} - \frac{1}{M}\right)$$

where r is the radius of the source scan path, $r_o$ is the radius of the field of view, M is the system magnification, k is a constant and $10 \geq k \geq 1/10$;
   means, operatively connected to said area detector for acquiring data from the area detector at intervals $\Delta$s; and
   a display operatively connected to said means for acquiring data for displaying a CT image based on the acquired data.

17. The system of claim 16 wherein $4 \geq k \geq \tfrac{1}{4}$.

18. The system of claim 17 wherein $(2)^{\frac{1}{2}} \geq k \geq 1/(2)^{\frac{1}{2}}$.

19. The system of claim 18 wherein $1.1 \geq k \geq 0.9$.

20. The system of claim 16 wherein said area detector is constructed such that $w_1 = w_2$ and equation I simplifies to equation II as follows:

$$\Delta s = k \cdot w_1 \left(\frac{r}{r_o} - \frac{1}{M}\right).$$

21. The system of claim 16 wherein said means for determining is a memory containing data representative of locations in trajectory s corresponding to the intervals $\Delta$s.

22. The system of claim 16 wherein said means for determining is operable to calculate data representative of locations in the trajectory s corresponding to the intervals $\Delta$s.

23. The system of claim 16 wherein said scanning means provides a trajectory which is a two cycle sinusoid on cylinder scan defined by equations III as follows:

$$x = r \cos \Theta$$

$$y = r \sin \Theta$$

$$z = A \sin 2\Theta$$

where r and A are respectively the radius and one-half the height of the cylinder and $\Theta$ is an angle within an xy plane of a point on the trajectory relative to the x axis such that equation II simplifies to equation IV as follows:

$$\Delta\Theta = k \cdot (1/2(w_1^2 + w_2^2))^{\frac{1}{2}} \left(\frac{r}{r_o} - \frac{1}{M}\right)/(r^2 + 4A^2\cos^2 2\Theta)^{\frac{1}{2}}$$

where values of $\Delta\Theta$ represent angular intervals relative to $\Theta$ at which data is to be acquired, and wherein said means for determining determines $\Delta$s by providing $\Delta\Theta$.

24. The system of claim 16 wherein said scanning means provides the trajectory s which is parameterized by general trajectory equations as follows:

$$x = f_x(u)$$

$y = f_y(u)$ $z = f_z(u)$ where u is a parameter used to define the trajectory, $f_x$, $f_y$, and $f_z$ are functions of u, and the intervals $\Delta s$ are determined by providing $\Delta u$, which are changes in the parameter u corresponding to the intervals $\Delta s$, using $$\Delta u = \frac{k \cdot (1/2(w_1^2 + w_2^2))^{\frac{1}{2}} \left(\frac{r}{r_o} - \frac{1}{M}\right)}{(F_x^2(u) + F_y^2(u) + F_z^2(u))^{\frac{1}{2}}}$$

where $F_x$, $F_y$, and $F_z$ are respectively the derivative functions relative to u of $f_x$, $f_y$, and $f_z$.

25. The system of claim 16 wherein said scanning means provides that the trajectory s is on a cylinder of radius r and defined by:

$x = r \cos \Theta$ $y = r \sin \Theta$ $z = f(\Theta)$ where $\Theta$ is an angle within an xy plane of a point on the trajectory relative to the x axis such that the intervals $\Delta s$ are determined by providing angular intervals $\Delta \Theta$ according to:

$$\Delta \Theta = \frac{k \cdot (1/2(w_1^2 + w_2^2))^{\frac{1}{2}} \left(\frac{r}{r_o} - \frac{1}{M}\right)}{(r^2 + F^2(\Theta))^{\frac{1}{2}}}$$

where F is the derivative function relative to $\Theta$ of f and wherein data is acquired at the angular intervals $\Delta \Theta$.

26. The system of claim 16 wherein the trajectory s is on a sphere of radius r and is defined by:

$x = r \cdot (1 - \frac{1}{3} \sin^2 2\Theta)^{\frac{1}{2}} \cos \Theta$ $y = r \cdot (1 - \frac{1}{3} \sin^2 2\Theta)^{\frac{1}{2}} \sin \Theta$ $z = r/(3)^{\frac{1}{2}} \sin 2\Theta$ where $\Theta$ is an angle within the xy plane of a point on the trajectory relative to the x axis such that the intervals $\Delta s$ are determined by providing angular intervals $\Delta \Theta$ according to:

$$\Delta \Theta = \frac{k \cdot (1/2(w_1^2 + w_2^2))^{\frac{1}{2}} (1 - 1/3\sin^2 2\Theta)^{\frac{1}{2}} \left(\frac{r}{r_o} - \frac{1}{M}\right)}{r(1/3 + 2\cos^2 2\Theta + 1/9 \cdot \sin^4 2\Theta)^{\frac{1}{2}}}$$

and wherein said means for acquiring data acquires data at the angular intervals $\Delta \Theta$.

27. The system of claim 16 wherein the trajectory s is on a sphere of radius r and is defined by:

$x = r \cos \Theta$ $y = r \sin \Theta$ $z = \Theta \cdot h / 2\pi$ where r and h are constants, $\pi$ is the circumference of a circle divided by its diameter, and $\Theta$ is an angle within the xy plane of a point on the trajectory relative to the x axis such that the intervals $\Delta s$ are determined by providing angular intervals $\Delta \Theta$ according to:

$$\Delta \Theta = \frac{k \cdot (1/2(w_1^2 + w_2^2))^{\frac{1}{2}} \left(\frac{r}{r_o} - \frac{1}{M}\right)}{(r^2 + (h/2\pi)^2)^{\frac{1}{2}}}$$

and wherein data is acquired at the angular intervals $\Delta \Theta$.

* * * * *